United States Patent [19]
Takeshima et al.

[11] Patent Number: 5,908,993
[45] Date of Patent: Jun. 1, 1999

[54] APPARATUS FOR MEASURING TOTAL SURFACE AREA OF A PORTION OF CATALYTIC METAL PARTICLES

[75] Inventors: Shinichi Takeshima, Susono; Toshiaki Tanaka, Numazu, both of Japan

[73] Assignee: Toyota Jidosha Kabushiki Kaisha, Aichi, Japan

[21] Appl. No.: 08/898,816

[22] Filed: Jul. 23, 1997

[30] Foreign Application Priority Data

Aug. 1, 1996 [JP] Japan .................................. 8-203796

[51] Int. Cl.$^6$ .................................................. G01N 15/00
[52] U.S. Cl. ................................................ 73/865.5; 73/38
[58] Field of Search ............................ 73/38, 53.01, 865.5

[56] References Cited

U.S. PATENT DOCUMENTS

| 4,566,326 | 1/1986 | Lowell ................................ 73/865.5 |
| 5,109,716 | 5/1992 | Ito et al. ............................. 73/865.5 |
| 5,513,515 | 5/1996 | Mayer ...................................... 73/38 |
| 5,591,897 | 1/1997 | Nakamura et al. ....................... 73/38 |
| 5,637,810 | 6/1997 | Conner, Jr. ......................... 73/865.5 |
| 5,744,699 | 4/1998 | Suzuki .................................... 73/38 |

FOREIGN PATENT DOCUMENTS 2552213  2/1990  Japan .

OTHER PUBLICATIONS

Gruber, Hans L. An Adsorption Flow Method for Specific Metal Surface Area Determination. Analytical Chemistry, vol. 34, No. 13, (Dec. 1962), pp. 1828–1831.

Loebenstein, William V., and Dietz, Victor R. Surface–Are Determination by Adsorption of Nitrogen from Nitrogen––Helium Mixtures. Journal of Research of the National Bureau of Standards. vol. 46, No. 1 (Jan. 1951), pp. 51–55.

*Primary Examiner*—George Dombroske
*Assistant Examiner*—Paul D. Amrozowicz
*Attorney, Agent, or Firm*—Kenyon & Kenyon

[57] ABSTRACT

According to the present invention, there is provided an apparatus for measuring total surface area of a portion of catalytic metal particles carried on the surfaces of pores in a carrier of a catalyst, comprising a device for supplying the pores with a first gas under a predetermined pressure to mask the surfaces of the catalytic metal particles carried on a first portion of the surfaces of said pores, which first portion has a radius less than a radius determined by the predetermined pressure of said first gas and a device for supplying said pores with a second gas which is to be adsorbed on the surfaces of said catalytic metal particles carried on a second portion of the surfaces of said pores, which second portion has a radius equal to or greater than the radius determined by the predetermined pressure, and is not masked by said first gas. Also included is a processor for calculating total surface area of said catalytic metal particles carried on said second portion of the surfaces of said pores by an amount which is adsorbed on said surfaces of said catalytic metal particles.

20 Claims, 4 Drawing Sheets

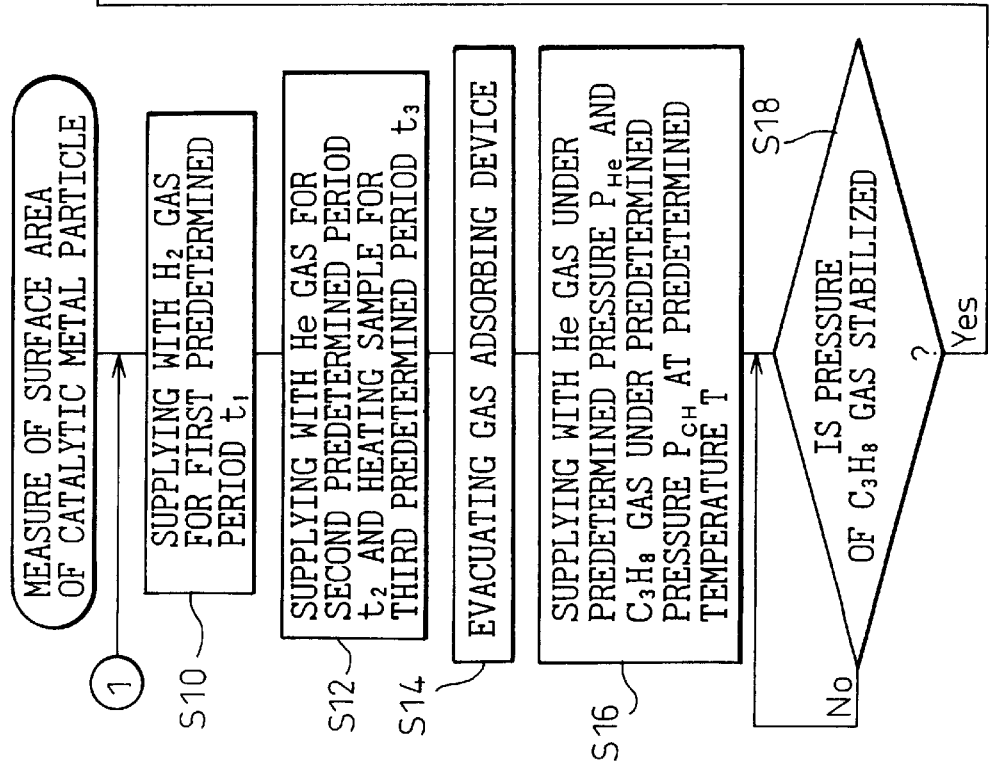

APPARATUS FOR MEASURING TOTAL SURFACE AREA OF A PORTION OF CATALYTIC METAL PARTICLES

BACKGROUND OF THE INVENTION

1. Field of the Invention

The invention relates to an apparatus for measuring the total surface area of catalytic metal particles.

2. Description of the Relates Art

A catalyst for purifying injurious gases in the exhaust gas discharged from an engine is known. The catalyst comprises a carrier having pores therein and catalytic metal particles carried on surfaces of the pores of the carrier. The character of the catalyst depends on total surface area of the catalytic metal particles per unit weight, i.e., a specific area and a distribution of the radii of the pores. For example, in Japanese Unexamined Patent Publication (Kokai) No. 2-55213, a specific surface area of a catalyst is measured by a BET type specific surface area measure, and the distribution of the radii of the pores is calculated or the basis of an adsorption isotherm and a relative pressure.

The character of the catalyst also depends on a distribution of the surface areas of the catalytic metal particles relative to the radii of the pores. However, the distribution can not be measured by the technique disclosed in Japanese Unexamined Patent Publication (Kokai) No. 2-55213.

SUMMARY OF THE INVENTION

Accordingly, the object of the invention is to provide an apparatus for measuring the total surface area of a portion of catalytic metal particles, which apparatus can measure a distribution of surface areas of the catalytic metal particles relative to the radii of the pores.

According to the present invention, there is provided an apparatus for measuring total surface area of a portion of the catalytic metal particles carried on the surfaces of pores in a carrier of a catalyst, comprising: means for supplying the pores with a first gas under a predetermined pressure to mask the surfaces of the catalytic metal particles carried on a first portion of the surfaces of said pores, which first portion has a radius less than a radius determined by the predetermined pressure of said first gas; means for supplying said pores with a second gas which is to be adsorbed on the surfaces of said catalytic metal particles carried on a second portion of the surfaces of said pores, which second portion has a radius equal to or greater than the radius determined by the predetermined pressure, and is not masked by said first gas; and means for calculating total surface area of said catalytic metal particles carried on said second portion of the surfaces of said pores by an amount of said second gas which is adsorbed on said surfaces of said catalytic metal particles.

Further, according to the present invention, said pores have a wedge-shaped cross section.

Further, according to the present invention, said second gas is supplied in the form of a pulse.

Further, according to the present invention, said second gas comprises CO gas.

Further, according to the present invention, said second gas comprises He gas.

Further, according to the present invention, said second gas in the form of pulse entrains with said He gas.

Further, according to the present invention, a purifying means is provided for purifying said surfaces of said catalytic metal particles before said first gas is supplied.

Further, according to the present invention, said purifying means comprises a device for supplying said pores with $H_2$ gas and means for heating said catalyst.

Further, according to the present invention, said first gas comprises saturated hydrocarbons or a noble gas.

Further, according to the present invention, said first gas is maintained at the predetermined pressure while said second gas is supplied.

According to the present invention, there is provided a method for measuring the total surface area of a portion of catalytic metal particles carried on surfaces of pores in a carrier of a catalyst, comprising: supplying the pores with a first gas under a predetermined pressure to mask the surfaces of the catalytic metal particles carried on a first portion of the surfaces of said pores, which first portion has a radius less than a radius determined by the predetermined pressure of said first gas; supplying the pores with a second gas which is to be adsorbed on the surfaces of said catalytic metal particles carried on a second portion of the surfaces of said pores, which second portion has a radius equal to or greater than the radius determined by the predetermined pressure, and is not masked by said first gas; and calculating the total surface area of said catalytic metal particles carried on said second portion of the surfaces of said pores by an amount of said second gas which is adsorbed on said surfaces of said catalytic metal particles.

Further, according to the present invention, said pores have a wedge-shaped cross section.

Further, according to the present invention, said second gas is supplied in the form of a pulse.

Further, according to the present invention, said second gas comprises CO gas.

Further, according to the present invention, said second gas comprises He gas.

Further, according to the present invention, said second gas in the form of pulse entrains with said He gas.

Further, according to the present invention, said surfaces of said catalytic metal particles are purified before said first gas is supplied.

Further, according to the present invention, said surfaces of said catalytic metal particles are purified by supplying said pores with $H_2$ gas and heating said catalyst.

Further, according to the present invention, said first gas comprises saturated hydrocarbons or a noble gas.

Further, according to the present invention, said first gas is maintained at the predetermined pressure while said second gas is supplied.

The present invention may be more fully understood from the description of the preferred embodiments of the invention set forth below, together with the accompanying drawings.

BRIEF DESCRIPTION OF THE DRAWINGS

In the drawings:

FIG. 6 is a flowchart of measuring a distribution of the surface areas of the catalytic metal particles relative to the radii of the pores.

DESCRIPTION OF THE PREFERRED EMBODIMENTS

Figure 1:
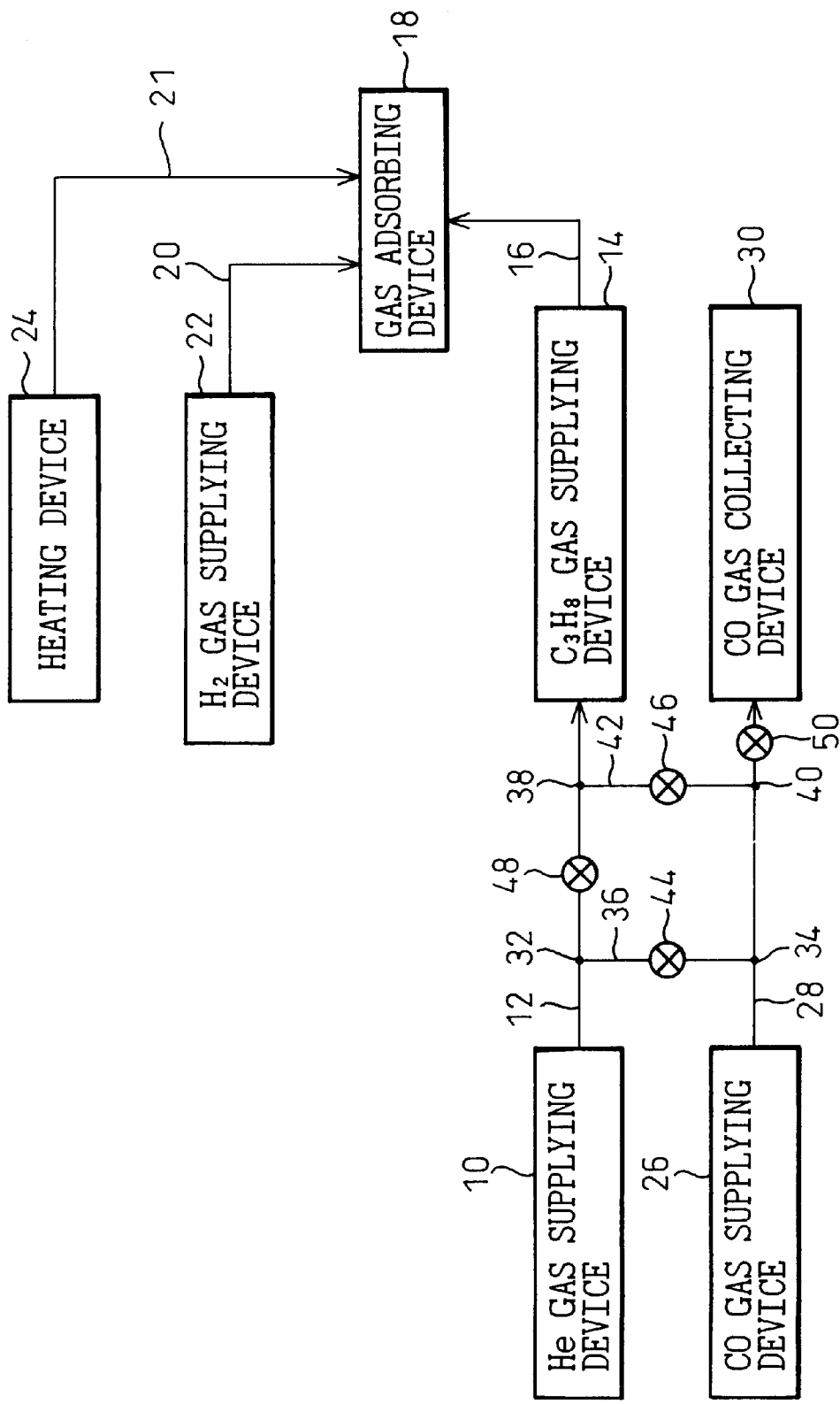
FIG. 1 is a view of the relationship among devices which constitute an apparatus for measuring total surface area of a portion of catalytic metal particles according to the invention.

The invention will be understood from the following description and by referring to the drawings. FIG. 1 shows a relationship between devices constituting an apparatus for measuring the total surface area of catalytic metal particles carried on the surfaces of pores in a carrier of a catalyst according to the invention. A device 10 for supplying helium (He) gas is connected to a device 14 for supplying $C_3H_8$ gas via a pipe 12. The $C_3H_8$ gas supplying device 14 is connected to a device 18 for masking the surfaces of the pores and the surfaces of the catalytic metal particles carried thereon with adsorbing gases via a pipe 16. A device 22 for supplying $H_2$ gas is connected to the gas adsorbing device 18 via a pipe 20. A heating device 24 is connected to the gas adsorbing device 18 via a pipe 21. A device 26 for supplying CO gas is connected to a device 30 for collecting CO gas via a pipe 28.

Note that the $C_3H_8$ gas supplying device 14 constitutes means for supplying with a first gas, the He gas supplying device 10 and the CO gas supplying device 26 constitute means for supplying a second gas, and the heating device 24 and the $H_2$ gas supplying device 22 constitute means for purifying the catalyst.

The pipes 12 and 28 are connected to each other via a pipe 36 and a pipe 42. One end of the pipe 36 is connected to the pipe 12 at a connecting point 32 thereof. The other end of the pipe 36 is connected to the pipe 28 at a connecting point 34 thereof. One end of the pipe 36 is connected to the pipe 12 at a connecting point 38 thereof downstream of the connecting point 32. The other end of the pipe 36 is connected to the pipe 28 at a connecting point 40 thereof downstream of the connecting point 34.

A pulse generating valve 44 is positioned on the pipe 36 while a pulse generating valve 46 is positioned on the pipe 42. A valve 48 for closing the pipe 12 between the connecting points 32 and 38 is positioned on the pipe 12 between the connecting points 32 and 38. Further, a valve 50 for closing the pipe 28 downstream of the connecting point 40 is positioned on the pipe 28 downstream of the connecting point 40. In this specification, the word "downstream" is associated with the flow direction of the gases from each gas supplying device to the gas adsorbing device.

Figure 2:
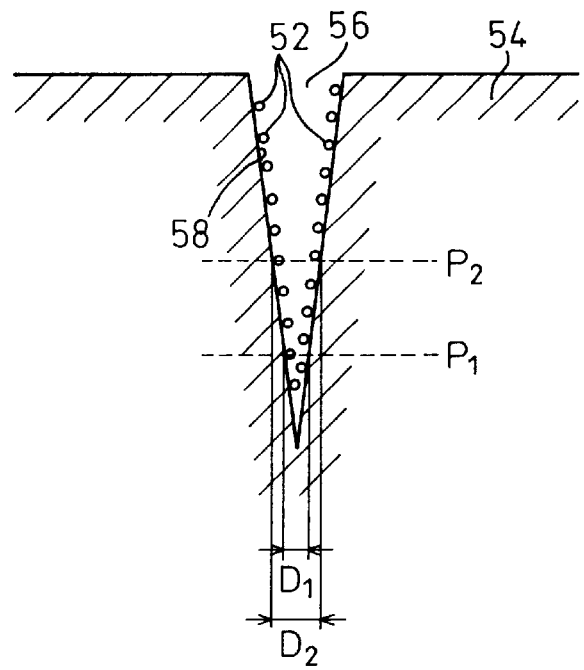
FIG. 2 is a view of a cross section of the catalyst.

Referring to FIG. 2, the catalyst comprises a carrier 54 which has pores 56 (In FIG. 2, only one is shown.), and a number of catalytic metal particles 52, such as Platinum, carried on a surface 58 of one of the pores 56. The pore 56 has a wedge-shaped cross section.

The process of measuring total surface area of a portion of catalytic metal particles according to the invention will be described below. A catalyst as a sample to be measured is positioned in the gas adsorbing device 18. Next, $H_2$ gas is supplied from the $H_2$ gas supplying device 22 to the gas adsorbing device 18 for a predetermined period $t_1$ to deoxidize the oxidized surfaces of the catalytic metal particles 52. Then, the catalyst is heated by the heating device 24 while He gas is supplied from the He gas supplying device 10 to the gas adsorbing device 18 for a predetermined period $t_2$ to purge $H_2$ gas from the pores 56 of the catalyst. Next, the gas adsorbing device 18 is evacuated to completely eliminate any gas adsorbed on the surfaces 58 of the pores 56 of the catalyst and the surfaces of the catalytic metal particles 52. Consequently, the surfaces 58 of the pores 56 of the catalyst and the surfaces of the catalytic metal particles 52 are purified.

After the purification, the gas adsorbing device 18 is maintained at a predetermined temperature T while He gas from the He gas supplying device 10 under a predetermined pressure $P_{He}$ at a constant flow rate, and $C_3H_8$ gas from the $C_3H_8$ gas supplying device 14 under a first predetermined pressure $P_{CH}=P_1$ at a constant flow rate are supplied into the gas adsorbing device 18 as the first processing gas. On the other hand, CO gas is supplied from the CO gas supplying device 26 into the CO gas collecting device 30 via the pipe 28. The valves 48 and 50 are open while the pulse generating valves 44 and 46 are closed.

The capillary condensation is known, in that vapor which is taken into the pores of the porous solid by the capillary phenomenon, is condensed into liquid. The relation $\log(p/P)=-2\sigma V/rRT$ is established when the vapor contacts the capillary which has a radius r, where $\sigma$ is a surface tension, V is a molecular volume, P is a vapor pressure, p is a vapor pressure of the liquid in the capillary, R is a gas constant, and T is an absolute temperature. Therefore, the narrower the capillary is, i.e., the smaller the radius r of the capillary is, the lower the vapor pressure of the liquid in the capillary is, i.e., the easier the vapor is condensed into a liquid in the capillary.

Therefore, during the supply of $C_3H_8$ gas into the gas adsorbing device 18 under the first predetermined pressure $P_1$, $C_3H_8$ gas is condensed by the capillary condensation in the pore 56 which has a radius less than $D_1$ which is determined by the predetermined pressure $P_1$. Therefore, the surface 58 of the pore 56 having the radius less than $D_1$, and surface of a first portion of the catalytic metal particles 52 carried thereon are masked by a liquid of $C_3H_8$.

Next, the valves 48 and 50 are closed and, at the same time, the pulsing valves 44 and 46 are opened while $C_3H_8$ gas is supplied into the gas adsorbing gas device 18 under the first predetermined pressure $P_1$. Therefore, He gas flows into the pipe 36. Then, He gas flows sequentially via the pipe 36, the pipe 28, the pipe 42 and the pipe 12, entrains with CO gas in the pipe 36 between the valve 44 and the connecting point 34, the pipe 28 between the connecting points 34 and 40, and the pipe 42 between the connecting point 40 and valve 46. Thereafter, the valves 48 and 50 are opened and the same time, the valves 44 and 46 are closed.

The above process of closing and opening the valves is repeated. Therefore, CO gas in the form of a pulse is supplied into the gas adsorbing device 18 as a second adsorbing gas.

The CO gas which is supplied into the gas adsorbing device 18 is adsorbed on the surface 58 of the catalytic metal particles 52 which are carried on a second portion of the surfaces of said pores, which second portion has a radius equal to or greater than the radius determined by the predetermined pressure and which is not masked.

Figure 3:
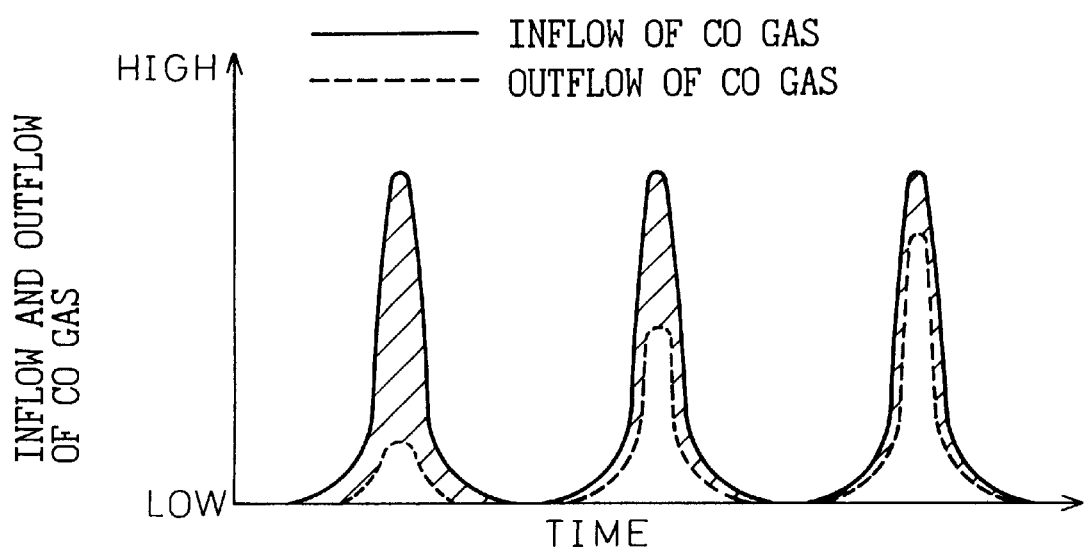
FIG. 3 is a view of the relationship between the time and the inflow amount of CO gas which is supplied into the sample gas adsorbing device and the outflow amount of CO gas which flows out of the sample gas adsorbing device in the form of pulse.

Referring to FIG. 3, the line shows an inflow amount of CO gas which is supplied into the gas adsorbing device 18 while the dot line shows an outflow amount of CO gas which flows out of the gas adsorbing device 18. The shaded portion of FIG. 3 shows an amount of CO gas which is adsorbed on the surface of the catalytic metal particles carried on the second portion of the surfaces of the pores. When CO gas is adsorbed on the entire non-masked surface of the catalytic metal particles, the inflow amount of CO gas is equal to the outflow amount of CO gas. The surface area of the catalytic metal particles carried on the surface of the second portion of the pores, which second portion has a radius equal to or greater than $D_1$, can be calculated by the total amount of CO gas which is adsorbed on the non-masked surface of the catalytic metal particles 52.

On measuring the total surface area of the catalytic metal particles carried on the surfaces of a fourth portion of the pores, which fourth portion has a radius equal to or greater than $D_2$ which is determined by a second predetermined pressure $P_2$, $H_2$ gas is supplied into the gas adsorbing device 18 for a first predetermined period $t_1$ in order to purify the surfaces 58 of the pores 56 and the surfaces of the catalytic metal particles 52 carried thereon. Next, He gas is supplied into the gas adsorbing device 18 for a second predetermined period $t_2$ while the sample is heated. Next, the gas adsorbing device 18 is evacuated. Next, $C_3H_8$ gas is supplied into the gas adsorbing device 18 at a second predetermined pressure $P_2$ to mask the surfaces 58 of a third portion of the pore 56, and the surfaces of the catalytic metal particles 52 carried on the surfaces 58 of the third portion of the pores 56, which third portion has a radius less than $D_2$ which is determined by the second predetermined pressure $P_2$. Next, CO gas in the form of a pulse is supplied into the gas adsorbing device 18 to be adsorbed on the non-masked surfaces of the catalytic metal particles 52. The surface area of the non-masked surface of the catalytic metal particles 52 can be calculated by the total amount of the CO gas which is adsorbed on the non-masked surfaces of the catalytic metal particles 52.

The above process of measuring the total surface area of a portion of the catalytic metal particles is repeated until the pressure of $C_3H_8$ becomes the vapor pressure $P_0$. Therefore, a distribution of the surface area of the catalytic metal particles relative to each radius of the pores can be measured.

Figure 4:
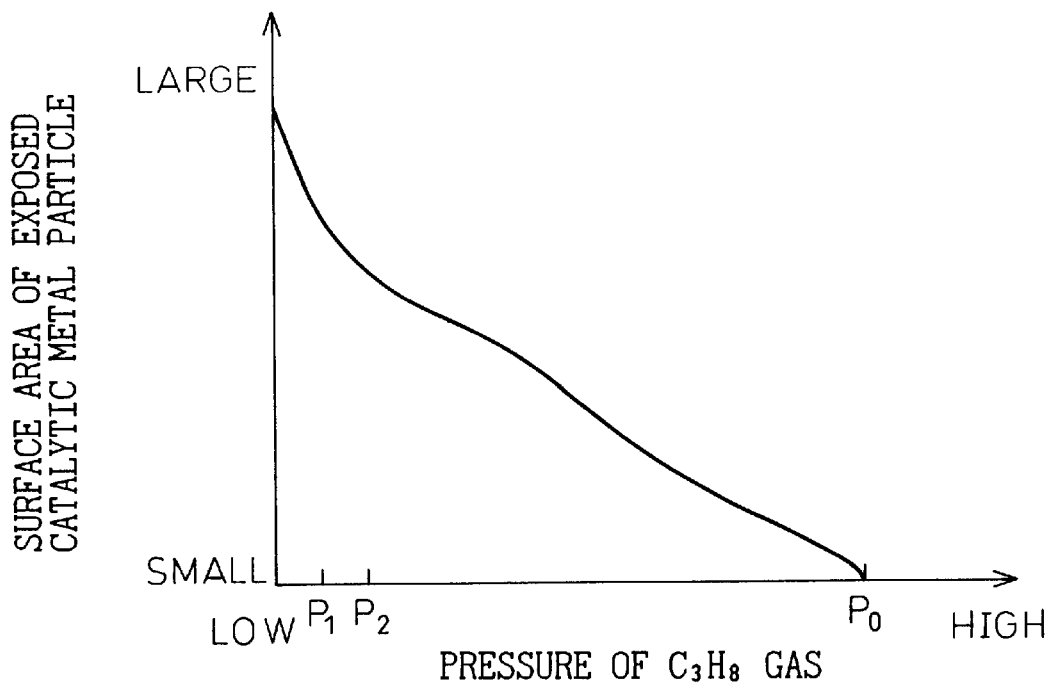
FIG. 4 is a view of the relationship between the supplying pressure of $C_3H_8$ gas and the surface area of the exposed surface of the catalytic metal particles.

FIG. 4 shows an example of the relation between the supplying pressure of $C_3H_8$ gas and the surface area of the exposed surface of the catalytic metal particles.

Figure 5:
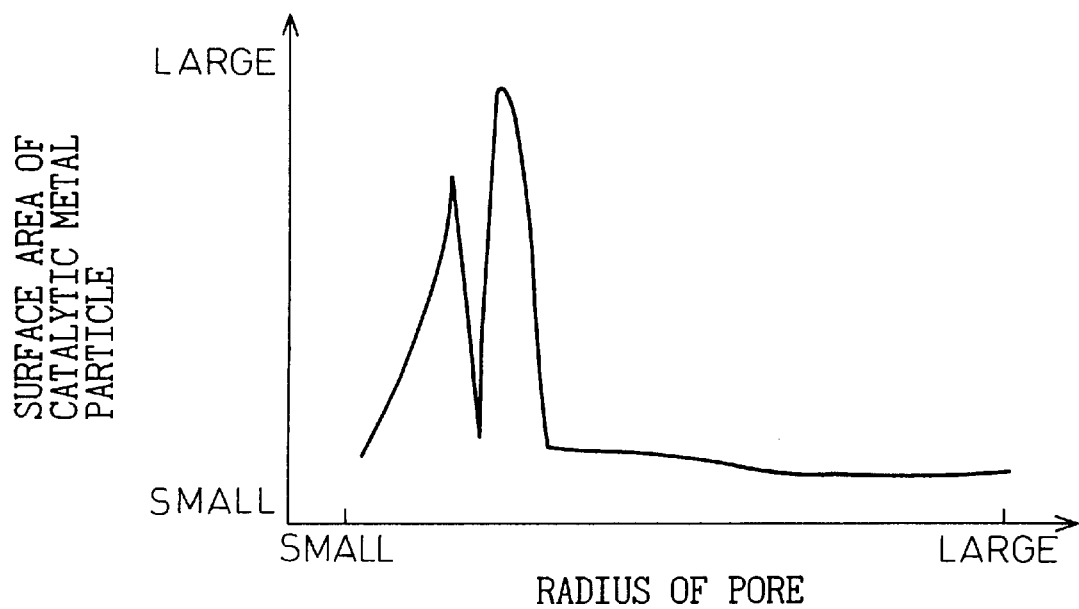
FIG. 5 is a view of the relationship between the radii of the pores determined by the supplying pressure of the $C_3H_8$ gas and the surface area of the catalytic metal calculated by the amount of the CO gas adsorbed on the catalytic metal.

FIG. 5 shows an example of the relation between the radius of the pore, which radius is determined by the supplying pressure of $C_3H_8$ gas and the surface area of the catalytic metal particles calculated by the amount of CO gas adsorbed on the catalytic metal particles.

According to the embodiment, the surface area of a portion of the catalytic metal particles carried on the surfaces of the pores can be calculated for every radius of the pores.

According to the embodiment, the flow rate of $C_3H_8$ gas and He gas which are supplied into the gas adsorbing device 18 are constant. Further, CO gas in the form of a pulse is entrained in the He gas. Therefore, the pressure of $C_3H_8$ gas which is supplied into the gas adsorbing device 18 is constant. Since the surfaces of the catalytic metal particles to be measured are kept masked, the surface area of the catalytic metal particles is exactly measured.

FIG. 6 is a flowchart of measuring a distribution of the surface area of the catalytic metal particles relative to the radius of the pores by using the apparatus for measuring the total surface area of a portion of the catalytic metal particles according to the invention. At step S10, $H_2$ gas is supplied into the gas adsorbing device 18 for a first predetermined period $t_1$. Next, at step S12, He gas is supplied into the gas adsorbing device 18 for a second predetermined period $t_2$ and the sample is heated for a third predetermined period $t_3$. Next, the gas adsorbing device 18 is evacuated. Next, at step S16, He gas under a predetermined pressure $P_{He}$, and $C_3H_8$ gas under a predetermined pressure $P_{CH}$ are supplied into the gas adsorbing device 18 at a predetermined temperature T. Next, at step S18, it is judged if the pressure of $C_3H_8$ gas is stabilized. When the pressure of $C_3H_8$ gas is stabilized, the routine proceeds to step S20, where CO gas in the form of pulse is supplied into the gas adsorbing device 18, and the routine proceeds to step S22. On the other hand, when the pressure of $C_3H_8$ gas is not stabilized, the routine returns to step S18.

At step S22, it is judged if the inflow rate $R_{in}$ of CO gas is equal to the outflow rate $R_{out}$ of CO gas ($R_{in}=R_{out}$). When $R_{in}=R_{out}$, the routine proceeds to step S24, where the surface area of a portion of the catalytic metal particles is calculated by the total amount of CO gas which is adsorbed on the surface of the portion of the catalytic metal particles, and the routine proceeds to step S26. On the other hand, when it is not $R_{in} \neq R_{out}$, the routine returns to step S22.

At step S26, it is judged if the pressure $P_{CH}$ Of $C_3H_8$ gas is equal to or greater than the predetermined pressure $P_0$ ($P_{CH} \geq P_0$). When $P_{CH} \geq P_0$, the processing cycle is ended. On the other hand, when $P_{CH} < P_0$, the routine proceeds to step S28, where the predetermined pressure $P_P$ is added to the pressure $P_{CH}$ of $C_3H_8$ gas, and the routine proceeds to step S10.

In the above embodiment, $C_3H_8$ gas is used as the first gas. However, a saturated hydrocarbon such as $C_4H_{10}$ gas or a noble gas such as xenon may be used as the first gas. $H_2$ gas may be used as the second adsorbing gas.

While the invention has been described by reference to specific embodiments chosen for purposes of illustration, it should be apparent that numerous modifications can be made thereto by those skilled in the art without departing from the basic concept and scope of the invention.

We claim:

1. An apparatus for measuring a total surface area of a portion of catalytic metal particles carried on surfaces of pores in a carrier of a catalyst, comprising:

means for supplying the pores with a first gas under a predetermined pressure to mask the surfaces of the catalytic metal particles carried on a first portion of the surfaces of said pores, which first portion has a radius less than a radius determined by the predetermined pressure of said first gas;

means for supplying the pores with a second gas which is to be adsorbed on the surfaces of said catalytic metal particles carried on a second portion of the surfaces of said pores, which second portion has a radius equal to or greater than the radius determined by the predetermined pressure, and is not masked by said first gas; and means for calculating the total surface area of said catalytic metal particles carried on said second portion of the surfaces of said pores by an amount of said second gas which is adsorbed on said surfaces of said catalytic metal particles.

2. A measuring apparatus according to claim 1, wherein each of said pores has a wedge-shaped cross section.

3. A measuring apparatus according to claim 1, wherein said second gas is supplied in the form of a pulse.

4. A measuring apparatus according to claim 1, wherein said second gas comprises CO gas.

5. A measuring apparatus according to claim 4, wherein said second gas comprises He gas.

6. A measuring apparatus according to claim 5, wherein said second gas in the form of pulse entrains with said He gas.

7. A measuring apparatus according to claim 1, wherein a purifying means is provided for purifying said surfaces of said catalytic metal particles before said first gas is supplied.

8. A measuring apparatus according to claim 7, wherein said purifying means comprises a device for supplying said pores with $H_2$ gas and means for heating said catalyst.

9. A measuring apparatus according to claim 1, wherein said first gas comprises a saturated hydrocarbon or a noble gas.

10. A measuring apparatus according to claim 1, wherein said first gas is maintained at the predetermined pressure while said second gas is supplied.

11. A method for measuring the total surface area of a portion of catalytic metal particles carried on surfaces of pores in a carrier of a catalyst, comprising:

supplying the pores with a first gas under a predetermined pressure to mask the surfaces of the catalytic metal particles carried on a first portion of the surfaces of said pores, which first portion has a radius less than a radius determined by the predetermined pressure of said first gas;

supplying the pores with a second gas which is to be adsorbed on the surfaces of said catalytic metal particles carried on a second portion of the surfaces of said pores, which second portion has a radius equal to or greater than the radius determined by the predetermined pressure, and is not masked by said first gas; and calculating the total surface area of said catalytic metal particles carried on said second portion of the surfaces of said pores by an amount of said second gas which is adsorbed on said surfaces of said catalytic metal particles.

12. A measuring method according to claim 11, wherein said pores have a wedge-shaped cross section.

13. A measuring method according to claim 11, wherein said second gas is supplied in the form of a pulse.

14. A measuring method according to claim 11, wherein said second gas comprises CO gas.

15. A measuring method according to claim 14, wherein said second gas comprises He gas.

16. A measuring method according to claim 15, wherein said second gas in the form of pulse entrains with said He gas.

17. A measuring method according to claim 11, wherein said surfaces of said catalytic metal particles are purified before said first gas is supplied.

18. A measuring method according to claim 17, wherein said surfaces of said catalytic metal particles are purified by supplying said pores with $H_2$ gas and heating said catalyst.

19. A measuring method according to claim 11, wherein said first gas comprises a saturated hydrocarbon or a noble gas.

20. A measuring method according to claim 11, wherein said first gas is maintained at the predetermined pressure while said second gas is supplied.

* * * * *